US008653214B2

(12) United States Patent
Venzmer et al.

(10) Patent No.: US 8,653,214 B2
(45) Date of Patent: Feb. 18, 2014

(54) SILICONE (METH)ACRYLATE PARTICLES, PROCESS FOR PREPARATION THEREOF AND USE THEREOF

(75) Inventors: Joachim Venzmer, Essen (DE); Jürgen Meyer, Essen (DE); Matthias Naumann, Mülheim an der Ruhr (DE)

(73) Assignee: Evonik Goldschmidt GmbH, Essen (DE)

( * ) Notice: Subject to any disclaimer, the term of this patent is extended or adjusted under 35 U.S.C. 154(b) by 786 days.

(21) Appl. No.: 12/327,175

(22) Filed: Dec. 3, 2008

(65) Prior Publication Data

US 2009/0149573 A1    Jun. 11, 2009

(30) Foreign Application Priority Data

Dec. 6, 2007    (DE) .......................... 10 2007 058 713

(51) Int. Cl.
 *C08F 30/08*    (2006.01)
(52) U.S. Cl.
 USPC ........................................................ 526/279
(58) Field of Classification Search
 USPC ........................................................ 526/279
 See application file for complete search history.

(56) References Cited

U.S. PATENT DOCUMENTS

| | | | |
|---|---|---|---|
| 3,615,972 A | 10/1971 | Morehouse, Jr. et al. | |
| 4,306,050 A | 12/1981 | Koerner et al. | |
| 4,761,454 A | 8/1988 | Oba et al. | |
| 4,946,893 A | 8/1990 | Saito et al. | |
| 5,176,960 A | 1/1993 | Shimizu et al. | |
| 5,523,373 A | 6/1996 | Esselborn et al. | |
| 5,977,282 A | 11/1999 | Ebbrecht et al. | |
| 6,753,399 B2 | 6/2004 | Inokuchi | |
| 2004/0029978 A1* | 2/2004 | Chane-Ching | 516/9 |
| 2004/0063818 A1 | 4/2004 | Silber et al. | |
| 2004/0156808 A1 | 8/2004 | Kazuhiko et al. | |
| 2006/0084758 A1 | 4/2006 | Morita | |
| 2007/0208109 A1 | 9/2007 | Kautz et al. | |
| 2008/0064782 A1 | 3/2008 | Doehler et al. | |

FOREIGN PATENT DOCUMENTS

| | | |
|---|---|---|
| DE | 10011564 C1 | 9/2001 |
| DE | 102004014704 A1 | 10/2005 |
| DE | 102004022406 A1 | 12/2005 |
| DE | 102004034740 A1 | 2/2006 |
| DE | 102004047708 A1 | 4/2006 |
| DE | 102004053314 A1 | 5/2006 |
| DE | 102005001040 A1 | 7/2006 |
| DE | 102005011785 A1 | 9/2006 |
| EP | 0079322 | 5/1983 |
| EP | 0319828 B1 | 6/1989 |
| EP | 0433727 B1 | 6/1991 |
| EP | 0487624 B1 | 6/1992 |
| EP | 0516057 B1 | 12/1992 |
| EP | 0631774 A1 | 1/1995 |
| EP | 0661334 B1 | 7/1995 |
| EP | 0744432 B1 | 11/1996 |
| EP | 0765896 B1 | 4/1997 |
| EP | 0822232 A2 | 2/1998 |
| EP | 0835897 A2 | 4/1998 |
| EP | 0852610 B1 | 7/1998 |
| EP | 0882105 B1 | 12/1998 |
| EP | 0999230 A2 | 5/2000 |
| EP | 1074575 B1 | 2/2001 |
| EP | 1130046 B1 | 9/2001 |
| EP | 1544232 A1 | 6/2005 |
| EP | 1595909 A1 | 11/2005 |
| FR | 2808704 | 11/2001 |
| JP | 2003002973 A | 1/2003 |
| JP | 2003301047 A | 10/2003 |
| JP | 2006 070378 * | 3/2006 |
| WO | WO2005108449 A1 | 11/2005 |
| WO | WO2006016968 A1 | 2/2006 |

OTHER PUBLICATIONS

Landfester, K., et al., "Polydimethyl Siloxane Latexes and Copolymers by Polymerization and Polyaddition in Miniemulsion", Polymer, 2005, pp. 9892-9898, 46.
Pickering, S.U., "Emulsions", Journal of the Chemical Society, Transactions, 1907, pp. 2001-2021, 91.
Binks, B., "Particles as Surfactants—Similarities and Differences", Current Opinion in Colloid & Interface Science, 2002, pp. 21-41, 7.
Hassander, H., et al., "The Mechanism of Emulsion Stabilization by Small Silica (LUDOX®) Particles", Colloids and Surfaces, 1989, pp. 93 105, 40, Elsevier Science Publishers B.V., Amsterdam.
Cauvin, S. et al., "Pickering Stabilized Miniemulsion Polymerization: Preparation of Clay Armoured Latexes", Macromolecules, 2005, pp. 7887-7889, 38(19), American Chemical Society, Washington, DC.

* cited by examiner

*Primary Examiner* — Kuo-Liang Peng
(74) *Attorney, Agent, or Firm* — Scully, Scott, Murphy & Presser, P.C.

(57) ABSTRACT

The present invention relates to silicone (meth)acrylate particles, to a process for preparing such silicone (meth)acrylate particles including the steps of:
a) obtaining an emulsion composed of water and an organic phase comprising organopolysiloxanes modified terminally and/or laterally with acrylate groups, and
b) polymerizing the inner phase to completion by means of a free-radical initiator, the free-radical initiator being added to the outer phase (aqueous phase) in a concentration of 0.1 to 40% by weight based on the inner phase, and to the use of the particles alone or in a mixture with further particles, pigments and/or further customary additives in the form of powders or dispersions in coating, adhesive or sealant materials, in polymers, in defoamers, in wetting and levelling aids, in cosmetic or pharmaceutical formulations and care products, in cleaning and detergent compositions, or in applications for modifying the interface properties of solid and liquid substrates, for example tactile properties, hydrophobization, or sliding and/or release properties.

21 Claims, No Drawings

SILICONE (METH)ACRYLATE PARTICLES, PROCESS FOR PREPARATION THEREOF AND USE THEREOF

FIELD OF THE INVENTION

The invention provides organopolysiloxane (meth)acrylate particles, the preparation thereof by means of suspension polymerization and the use thereof.

BACKGROUND OF THE INVENTION

Fine powders composed of silicone elastomers already find use as additives in cosmetics and toiletries, for example as a matting agent, as an absorber for sebum or for generating a silky skinfeel, as additives for improving the mechanical properties of polymers and lacquers or coating materials, for example for increasing abrasion or scratch resistance and also impact resistance, and also as antiblocking agents for improving the lubricant properties of a wide variety of different surfaces, as flow or dispersing aids in powders, as additives in toners, and as a mild abrasive in washing and care formulations.

Several methods are known for the preparation of such particles. In principle, irregularly shaped silicone elastomer particles can be obtained by grinding operations of a particular bulk elastomer, but spheroidal or spherical particles generally offer performance advantages, in particular when attractive tactile properties of the particle-additized minerals and formulations are desired. Typically, such particles are prepared by crosslinking reactions within reactant droplets or growth/application of a polymer on to a particle core. Crosslinking reactions may be hydrosilylation reactions, condensation reactions, dehydrogenative coupling reactions or free-radical polymerizations.

Silicone particles from hydrosilylations are described, for example, in U.S. Pat. No. 4,761,454, JP 2003301047 and EP 1 074 575, hydrolysis and condensation reactions for preparing silicone particles can be found in EP 1 130 046, WO 2006/016968, JP 2003002973, U.S. Pat. No. 6,753,399, EP 0 765 896 and EP 0 744 432, whereas U.S. Patent Application Publication No. 2004/0156808 describes a dehydrogenative coupling reaction for this purpose. Finally, DE 10 2004 053 314 describes copolymers obtainable by means of free-radical polymerizations.

Miniemulsion polymerization of silicone acrylates to give nanoscale particles using a conventional emulsifier and a common molecular free-radical initiator, for example AIBN, is known from the literature ("Polydimethyl Siloxane Latexes and Copolymers by Polymerization and Polyaddition in Miniemulsion", Katharina Landfester, Ute Pawelzik, Markus Antonietti, Polymer, 46 (2005), 9892-9898). However, the process described in the prior art does not afford microscale particles which possess the desired performance properties, for example such particles cannot achieve good skinfeel which is desired for personal care applications.

Aqueous emulsions stabilized in the solid state were described in 1907 by S. U. Pickering ("Emulsions", Spencer Umfreville Pickering, Journal of the Chemical Society, Transactions (1907), 91, 2001-2021) and are considered to be particularly stable against coalescence. For example, DE 10 2004 014 704 describes the preparation of emulsions stabilized with pyrogenic particles. A good overview of the properties of such stabilizing solid particles can be found in "Particles as surfactants—similarities and differences" by Bernhard P. Binks (Current opinion in colloid & interface science, 7 (2002), 21-41). The prior art also includes so-called "Janus particles", amphiphilic particles with a hemispherically modified surface, as described, for example, in FR 2 808 704. Particularly suitable particles for emulsion stabilization are nanoscale, predominantly inorganic particles, for example silica particles, which are commercially available as "LUDOX®" in the form of aqueous sols and dispersions from Grace Davison. U.S. Pat. No. 3,615,972 describes the use of LUDOX® particles for emulsion stabilization of methyl methacrylate with subsequent polymerization. The mechanism discussed in the literature for the stabilizing action is the agglomeration of the particles and the enrichment of the agglomerates at the water/oil interface ("The mechanism of emulsion stabilization by small silica (LUDOX®) particles", Helen Hassander, Beatrice Johansson, Bertil Törnell, Colloids and Surfaces, 40, (1989), 93-105).

The suspension polymerization of Pickering emulsions of sparingly water-soluble or water-insoluble reactants must, according to the present state of the art, be started by means of a free-radical initiator dissolved in the oil phase; the use of water-soluble free-radical initiators, for example with styrene as the sole monomer, leads to incomplete reaction and coagulation ("Pickering stabilized miniemulsion polymerization: Preparation of clay armoured latexes", Severine Cauvin, Patrick J. Colver, and Stefan A. F. Bon, Macromolecules 2005, 38, 7887-7889). A disadvantage of a suspension polymerization that is initiated with a molecular free-radical initiator is that reaction products of the free-radical initiator remain in the polymer and can become perceptible, for example, through odor nuisance or else through irritant or toxic properties.

The prior art processes described for preparing silicone particles include hydrosilylation, free-radical polymerization, dehydrogenative coupling or condensation of emulsified precursors, spray processes, and the injection of the precursors into a suitable media with subsequent immediate crosslinking.

The particles thus prepared predominantly have the disadvantage that they are not obtained as a free-flowing powder and are therefore difficult to handle, i.e., for example, difficult to dose, and are homogenizable in the particular formulations only with a high level of complexity. In addition, the particles prepared in the prior art usually contain proportions of crosslinking catalysts, often including elements of transition group 8 of the Periodic Table of the Elements, emulsifiers and possibly further processing aids. In cosmetic formulations, and also cleaning and care products, this is undesired or at least problematic.

A further disadvantage of the particles prepared according to the prior art is that polydimethylsiloxane-like particle surfaces can be modified only with difficulty.

However, such modification is often desired in order to be able to adapt the particles to the different technical requirements, i.e., for example, to enable their attachment to various matrices or to facilitate or actually make possible processability into formulations.

Some of these disadvantages can be overcome by composite particles. Composite particles refer here to core-shell particles, and particles into which additional solids have been incorporated.

For example, U.S. Pat. No. 4,946,893 (EP 0 319 828) describes the preparation of silicone particles filled with inorganic particles by means of a hydrosilylation reaction in aqueous phase, and U.S. Pat. No. 5,176,960 describes the preparation of highly filled, mechanically durable silicone particles by means of mixing hydrophobized $SiO_2$ with a diorganopolysiloxane and subsequent curing by spray-drying.

In contrast, core-shell particles allow modifications, in some cases controlled, of surface properties, which influence the desired performance properties.

According to the preparation process and use of the core-shell particles, their particle size may be within the nanometer or micrometer range. Core-shell particles can be prepared by literature processes; for instance, EP 0 661 334 describes silicone particles surface-coated with an organopolysilsesquioxane resin and the preparation thereof, U.S. Patent Application Publication No. 2006/0084758 describes the preparation of silicone particles surface-modified with smaller silicone particles, and silicone particles coated subsequently with $SiO_2$ from the aqueous phase can be found in EP 0 079 322, and EP 0 516 057. In addition, EP 0 079 322 describes silicone particles surface-coated with $SiO_2$ with the aid of an oily phase. Core-shell particles with a silicone polymer core and organopolymer shell are described in DE 10 2004 047 708 and DE 10 2004 022 406 (use in aqueous coating materials in EP 0 882 105, and in powder coatings in EP 0 852 610).

Moreover, there are numerous documents which relate to core-shell structures with an inorganic core and silicone shell, for example EP 0 822 232 and PP 0 433 727.

A disadvantage of these prior art processes for obtaining core-shell particles is that they are time-consuming and energy-intensive, multistage processes.

SUMMARY OF THE INVENTION

The present invention provides silicone (meth)acrylate particles which do not have one disadvantage or a plurality of disadvantages of prior art particles. Moreover, the present invention provides an alternative process which is preferably advantageous in terms of process economics. In some embodiments of the invention, the particles prepared have a spherical morphology and are free-flowing as a powder. In further embodiments of the invention, the particles prepared are substantially free of emulsifiers, crosslinking catalysts—in particular catalysts containing elements of transition group 8 of the Periodic Table of the Elements and also tin salts—and further processing aids. In yet further embodiments of the invention, the inventive particles are capable of undergoing an additional, subsequent and in particular simple modification of the particle surfaces, which can serve for compatibilization with different matrices or media, and/or for attachment to these matrices.

The silicone (meth)acrylate particles of the present invention are prepared by suspension polymerization of an aqueous emulsion (which may be stabilized in the solid state) of a suitable mono- or oligomer or macromonomer of a (meth) acrylate group-modified organosiloxane by means of a preferably water-soluble free-radical initiator added to the aqueous phase.

It has been found that, surprisingly, it is possible, in a suspension polymerization, to polymerize an aqueous emulsion of silicone (meth)acrylates and optionally added organic comonomers and/or further substances with an inorganic free-radical initiator dissolved in the aqueous phase to give spherical particles, without coagulation occurring, as described in the prior art for conventional unsaturated monomers (e.g., styrene, and methyl methacrylate). It is possible in the present invention to use either Pickering emulsions or conventional emulsions stabilized by molecular emulsifiers and/or surfactants.

The invention therefore provides a process for preparing silicone (meth)acrylate particles, which is characterized in that an aqueous emulsion comprising a monomeric silicone (meth)acrylate and optionally an organic unsaturated comonomer, and also an emulsifier and one or more coemulsifiers which stabilize the emulsion, is polymerized using a free-radical initiator added to the aqueous phase.

The present invention likewise provides silicone (meth) acrylate particles thus prepared and the use thereof.

The process according to the invention has the advantage that no reaction products of the initiator remain in the polymer when the polymerization is initiated by means of a water-soluble free-radical initiator, as is the case, for example, for oil-soluble free-radical initiators. This is advantageous for applications in the sectors of cosmetics, food packaging, medical products, etc.

The process according to the invention also has the advantage that no conventional emulsifiers, which might be disruptive later in applications and would therefore have to be removed again in a complicated manner, are needed in the preparation of the silicone (meth)acrylate composite particles by means of a suspension polymerization of Pickering emulsions.

Moreover, the inventive core-shell silicone (meth)acrylate particles or those prepared in accordance with the invention may have good free flow, such that no subsequent surface treatment is needed for this purpose.

DETAILED DESCRIPTION OF THE INVENTION

The process according to the invention for preparing inventive silicone (meth)acrylate particles and the use thereof are described by way of example hereinafter, without any intention that the invention be restricted to these illustrative embodiments.

When ranges, general formulae or compound classes are specified hereinafter, these shall encompass not just the particular ranges or groups of compounds which are mentioned explicitly but also all subranges and subgroups of compounds which can be obtained by selecting individual values (ranges) or compounds. When documents are cited in the context of the present description, their content shall be incorporated fully into the disclosure-content of the present invention. When compounds, for example organomodified polysiloxanes, which may have different units more than once, are described in the context of the present invention, these units may be present in these compounds in random distribution (random oligomer or polymer) or in ordered form (block oligomer or block polymer). Figures regarding the number of units in such compounds should be interpreted as the mean averaged over all appropriate compounds.

The process according to the invention for preparing silicone (meth)acrylate particles comprises:

a) obtaining an emulsion composed of water and an organic phase, said organic phase comprising at least one organopolysiloxane which has been modified terminally and/or laterally with (meth)acrylate groups and is of the general formula (I)

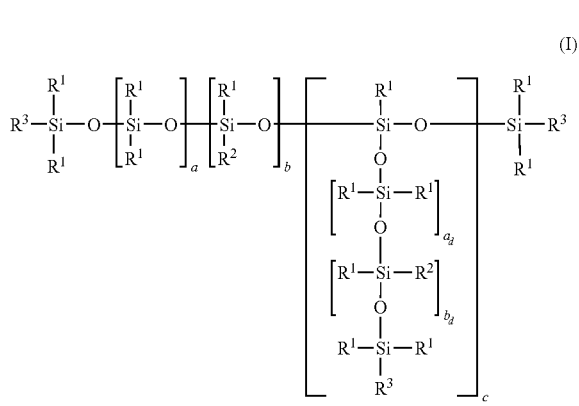

(I)

where
$R^1$ are identical or different radicals selected from linear or branched, saturated, monounsaturated or polyunsaturated, linear, cyclic or branched alkyl, alkoxy, polyalkoxy, hydroxyalkyl, hydroxyalkoxy, alkenyl, especially vinyl, aryl, aryloxy, hydroxyaryl, hydroxyaryloxy, alkaryl, alkaryloxy, hydroxyalkaryl, hydroxyalkaryloxy, aralkyl, aralkoxy, hydroxyaralkyl or hydroxyaralkoxy radicals which optionally contain one or more ether or ester bridges and have 1 to 20 carbon atoms, preferably identical or different radicals selected from linear or branched, saturated, mono- or polyunsaturated, linear, cyclic or branched alkyl, aryl, alkaryl or aralkyl radicals which optionally contain one or more ether or ester bridges and have 1 to 20 carbon atoms, preferably methyl or phenyl radicals,
$R^2$ are identical or different divalent, optionally OH-functionalized hydrocarbon radicals which optionally contain one or more ether or ester bridges, are bonded to the silicon atom via an Si—C linkage or an Si—O—C linkage, have 1 to 20 carbon atoms and to which are bonded, via ester bonds, 1 to 5 acrylic acid and/or methacrylic acid units and optionally monocarboxylic acid units having 2 to 10 carbon atoms, which are free of double bonds capable of polymerization, preferably linear or branched, aliphatic, aromatic or cyclic hydrocarbon bridges which may be interrupted by one or more ether and/or ester functions and may optionally bear one or more OH functions,
$R^3$ are identical or different $R^1$ or $R^2$ radicals,
a is 0 to 1000,
b is 0 to 200,
c is 0 to 200, preferably c=0,
$a_d$=0 to 1000,
$b_d$=0 to 200,
where the index d, when c>0, is an integer>0,
with the proviso that when b and c=0, $R^3$ must not be selected from the same group as $R^1$, or mixtures thereof,
with addition of at least one emulsifier, preferably of a solid-state emulsifier (particulate emulsifier), and optionally of one or more coemulsifiers, where the organic phase forms the inner phase of the emulsion, and
b) polymerizing the inner phase to completion in the presence of a free-radical initiator which is added to the outer phase (aqueous phase) in a concentration of 0.1 to 40% by weight, preferably 0.5 to 25% by weight and more preferably 1 to 10% by weight, based on the inner phase.

The polymerization to completion is thus effected in the form of a suspension polymerization.

The numerical values for a, b and c are preferably statistical mean values. The index d is an integer index term (serial variable).

The hydrocarbon bridges of formula (I) specified in $R^2$ may, for example, be alkylene, alkenylene, alkoxylene, polyalkoxylene, hydroxyalkylene, hydroxyalkoxylene, arylene, aryloxylene, hydroxyarylene, hydroxyaryloxylene, alkylarylene, alkaryloxylene, hydroxyalkarylene, hydroxyalkaryloxylene, aralkylene, aralkoxylene, hydroxyaralkylene or hydroxyaralkoxylene radicals.

The emulsifiers used in the present invention may be all customary emulsifiers. The emulsifiers may be anionic, cationic or nonionic surface-active substances.

Typical emulsifiers are, for example, alkyl sulphates, preferably with a chain length of 10 to 18 carbon atoms, alkyl and aryl ether sulphates, preferably with 10 to 24 carbon atoms in the hydrophobic radical and with preferably up to 40 ethylene oxide or propylene oxide units, alkyl- and alkylarylsulphonates with preferably 10 to 24 carbon atoms, alkyl diphenyl oxide disulphonates, oleic sulphonates, esters and monoesters of sulphosuccinic acid with monohydric alcohols or alkylphenols, alkyl and alkenyl carboxylates preferably having a chain length of 10 to 18 carbon atoms, alkyl polyglycol ethers and alkylaryl polyglycol ethers having preferably in each case 4 to 40 ethylene oxide units, alkyl and alkenyl alcohols with preferably 12 to 20 carbon atoms, ethoxylated alkyl and alkenyl alcohols with preferably 12 to 20 carbon atoms, and ethoxylated alkylphenols. Suitable emulsifier systems for cosmetic applications are especially those which typically serve for emulsification of silicone oils, as supplied, for example, by Evonik Goldschmidt GmbH under the names TEGO® Care Pt 4 or ABIL® Care 85. In particular, emulsifiers and surfactants known from cosmetic applications can be used, as detailed, for instance, in DE 10 2005 011785 A1.

It may be advantageous when, in step a), an emulsion stabilized in the solid state is obtained. To this end, the emulsifiers used may be nanoscale particulates which are preferably nanoscale in at least one dimension or nanostructured particles or nanoobjects, which are more preferably selected from the group of metal oxides, mixed oxides, nitrides, hydroxides, carbonates, silicates, silicone resins, silicones and/or organic polymers, which are preferably at least partly hydrophobized, for example with at least one compound from the group of silanes, siloxanes, quaternary ammonium compounds, cationic polymers and fatty acids or anions thereof. By virtue of the use of particulate emulsifiers, it is possible by the inventive process to prepare silicone acrylate composite particles, especially those of the core-shell type. Such core-shell type composite particles comprise the polymerized silicone acrylate (of the invention) in the core and the particulate emulsifiers as the shell. In the context of the present invention, nanoobjects are understood to mean materials which are nanoscale in one, two or three external dimensions; preferably, at least one dimension has a size of 1 to 100 nm; for example nanoplatelets, nanorods and nanoparticles. In the present invention, nanostructured particles refer to materials or particles which have an inner nanoscale structure. Typical representatives are, for example, aggregates and agglomerates of nanoobjects.

Particularly preferred particulate emulsifiers have a mean primary particle size in at least one dimension of less than 1000 nm, preferably less than 500 nm and more preferably from 1 to 100 nm. The primary particle size can be determined in a known manner. The primary particle size is preferably determined by the optical evaluation of a transmission electron micrograph.

The particulate emulsifiers can be used in the process according to the invention as such, or in the form of dispersions or sols, especially aqueous dispersions or sols.

Especially in the case of the use of particulate emulsifiers, it may be advantageous when, in step a) of the process according to the invention, the preparation of the emulsion is carried out with addition of one or more coemulsifiers. The coemulsifiers used in the process according to the invention may especially be those compounds which interact with the solid-state emulsifier particles, preferably those which attach to hydrophobizing solid-state emulsifier particles. In the inventive process, the coemulsifiers used may especially be compounds selected from the group of cationic surfactants. The cationic coemulsifiers used may especially be cationic ammonium compounds. Such compounds are obtainable, for example, under the trade names VARISOFT® 470 P, VARISOFT® TC-90, VARISOFT® 110, AROSURF® TA-100, ADOGEN® 442-100 P, ADOGEN® 432, ADOGEN® 470, ADOGEN® 471, ADOGEN® 464, VARIQUAT® K 300, VARIQUAT® B 343, VARIQUAT® 80 ME, REWOQUAT® 3690, REWOQUAT® WE15, REWOQUAT® WE18, REWOQUAT® WE 28 or REWOQUAT® CR 3099 from Evonik Goldschmidt GmbH. In the inventive process, preference is given to using cetyltrimethylammonium bromide or chloride as the cationic coemulsifier.

Also, in the inventive process, the silicone (meth)acrylates of formula (I) that are employed are preferably those in which more than 70%, more preferably more than 90%, most preferably, of the $R^1$ radicals in formula (I) are methyl groups.

The $R^2$ radicals in the general formula (I) are preferably selected from the group of the radicals of the formulae (IIa) to (IIj)

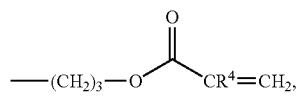
(IIa)

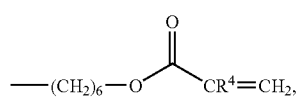
(IIb)

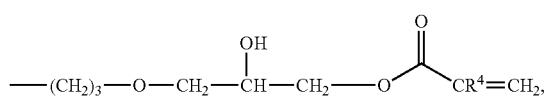
(IIc)

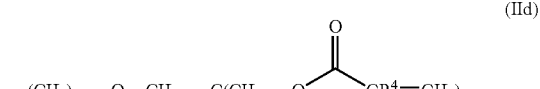
(IId)

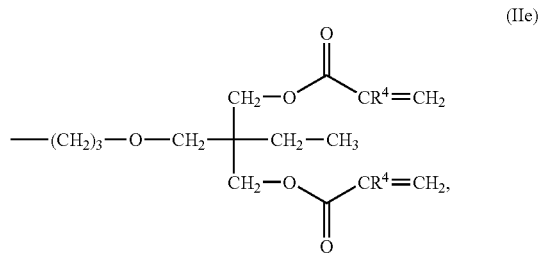
(IIe)

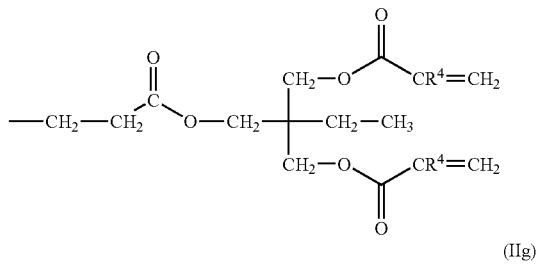
(IIf)

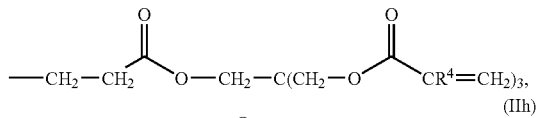
(IIg)

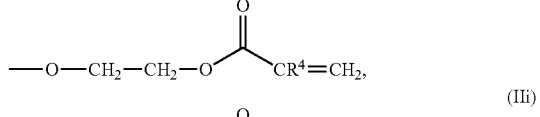
(IIh)

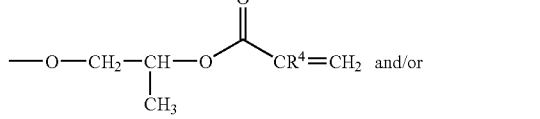
(IIi) and/or

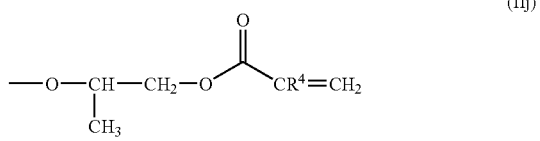
(IIj)

It is particularly preferred when $R^2$ is one of the radicals specified and the $R^4$ radical is hydrogen or a methyl group. In a highly preferred embodiment of the inventive process, use is made of silicone (meth)acrylates of formula (I) in which the $R^1$ radicals are methyl groups in the proportions specified above, the $R^2$ radicals are selected from the radicals of the formulae IIa to IIj, and the $R^4$ radical is hydrogen or a methyl group.

It may be advantageous when silicone (meth)acrylates of formula (I) in which the variable 'a' assumes a value of 0 to 500, preferably of 2 to 250, are used.

It may equally be advantageous when silicone (meth)acrylates of formula (I) in which the variable 'b' assumes a value of 0 to 100, preferably 1 to 50 and preferentially 3 to 25 are used.

It may also be advantageous when silicone (meth)acrylates of formula (I) in which the variable 'c' assumes a value of 0 to 100, preferably of 0 to 50, preferentially 0, are used.

It may be particularly advantageous when silicone (meth)acrylates of formula (I) in which the variable 'a' assumes a value of 0 to 500, preferably of 2 to 250, the variable 'b' assumes a value of 0 to 100, preferably 1 to 50 and more preferably 3 to 25, and the variable 'c' assumes a value of 0 to 100, preferably of 0 to 50, preferably 0, and $a_d$ and $b_d$ are defined correspondingly to a and b, are used.

The silicone (meth)acrylates used may especially be the products, TEGO® RC 705, 706, 708, 709, 710, 711, 712, 715, 716, 719, 726, 902, 2015 or TEGO® Rad 2100, 2200 N (silicone polyether acrylate), 2250 (silicone polyether acrylate), 2300 (silicone polyether acrylate), 2350 (silicone polyether acrylate), 2500 (acrylic-modified polydimethylsiloxane), 2600 (acrylic-modified polysiloxane), 2650 (acrylic-modified polysiloxane) or 2700 (acrylic-modified polysiloxane), obtainable from Evonik Goldschmidt GmbH.

In the process according to the invention, it is possible to use the silicone (meth)acrylates of the formula (I) individually or as mixtures, especially as random mixtures. In the process according to the invention, preference is given to using mixtures of silicone (meth)acrylates of the formula (I) in which the silicone (meth)acrylates differ with regard to their structure and/or their molecular weight.

It may be advantageous when, before step b), comonomers, especially comonomers having ethylenically or vinylically unsaturated groups, are added to the organic phase. Such comonomers may, for example, be mono- or poly(meth)acrylated organic mono- or oligomers, as sold, for example, under the group names LAROMER® (BASF AG), EBECRYL® (Cytec Surface Specialties) or DESMOLUX® (Bayer Material Science). Ethylenically mono- or polyunsaturated organic mono- or oligomers shall also be understood to mean ethylenically unsaturated organopolysiloxanes preferably bearing vinylic groups. Preference is given to adding the further comonomers before step a).

On completion of polymerization in step b), the organic comonomers may either have reacted to be incorporated covalently into the polysiloxane (meth)acrylate network or be present as a separate network. Mixed forms of these described limiting cases are equally possible and form part of this invention.

In the process according to the invention, before step b), preferably before step a), organopolysiloxanes which contain cationic groups and which may also bear reactive groups, for example vinylic groups, ethylenically unsaturated groups or epoxy groups, may be added to the organic, inner phase. The organopolysiloxanes which contain cationic groups and which may also bear reactive groups, for example vinylic groups, ethylenically unsaturated groups or epoxy groups are preferably added in a concentration of up to 25% by weight, preferably up to 10% by weight, more preferably up to 5% by weight, based on the overall reaction mixture.

In this way, it is possible to obtain cationic particles through which both good adhesion to specific substrates and electrostatic or electrosteric stabilization of dispersions can be achieved. Examples of such organopolysiloxanes which bear cationic groups are, for example, ABIL® Quat 3272 and ABIL® 3474 (Evonik Goldschmidt GmbH).

Optionally, further components may be added to the organic phase in step a). The further components may be dissolved or dispersed in the organic phase or the mixture in step a). Such further components may be functional components or nonfunctional components. The further components may especially be dispersible solids, for example inorganic particles and/or fibres, for example those of the metal oxides, mixed oxides, nitrides, hydroxides, carbonates, silicates, pigments, carbon blacks, elements or alloys, and/or organic particles and/or fibres, for example those composed of silicone resins, silicones or organic polymers or biopolymers, preferably with the proviso that the fillers are different from the emulsifiers used. Dispersible solids may, for example, be precipitated silica, diatomaceous earth (Kieselguhr), fumed silica, quartz flour, titanium dioxide, zinc oxide, cerium oxide, iron oxide, carbon black, graphite, carbon nanotubes or fibres, aluminosilicates, alkaline earth metal carbonates, aluminium trihydroxide, magnesium dihydroxide, or other customary solids known from the prior art, and any of the substances mentioned after surface modification with organosilicon compounds such as trimethylchlorosilane, hexamethyldisilazane, (meth)acryloyloxypropyltrialkoxysilanes, aminopropyltrialkoxysilanes, polydimethylsiloxanes, polysiloxanes which bear Si—H groups, or pure carboxylic acids, chelating agents or fluoropolymers. These solids may serve, for example, as fillers to achieve particular mechanical properties, as UV stabilizers, as pigments, as antistatic additives, or to achieve ferromagnetic properties.

In the process according to the invention, the organic phase may also include substances which may optionally be released from the particles, preferably over a prolonged period. Such substances may, for example, be cosmetic oils and active ingredients, fragrances, active pharmaceutical ingredients, active antimicrobial ingredients, including, for example, silver and silver compounds, and also dyes and preservatives.

It may be advantageous when, in step a) of the process according to the invention, an emulsion whose mean droplet size is adjusted to 0.01 to 1000 µm, preferably 0.1 to 500 µm and more preferably 1 to 100 µm, is obtained.

The droplet size can be estimated with the aid of light microscopy (down to approximately 1 µm as the lower limit) by measuring the smallest and largest droplet diameter in each case in the field of view; at least 10×10 droplets should be present in the field of view. In addition, it is possible to determine the droplet size distributions by the methods of static light scattering and of dynamic light scattering which are familiar to those skilled in the art. This is also true for dispersions of particles polymerized to completion; in addition, the particle size distribution can be determined by means of scanning electron micrographs or transmission electron micrographs, which are familiar to those skilled in the art.

The emulsion is preferably prepared in step a) by passing the mixture comprising organic and aqueous phase through and dispersing the mixture in at least one interaction chamber, preferably with a capillary thickness (internal diameter) of 50 to 500 µm, and preferably at a pressure of 50 to 1000 bar, preferably 100 to 800 bar, more preferably 200 to 600 bar, and then decompressing the mixture to ambient pressure, for example into an outlet reservoir. This preferably establishes one of the abovementioned preferred droplet sizes. It may be advantageous when two or more interaction chambers connected in series are used. In this way, the desired droplet size can be established more easily. The preparation of emulsions in interaction chambers is described in detail in U.S. Patent Application Publication No. 2004-0063818 and DE 100 11 564, to which explicit reference is made. A suitable instrument for preparing the emulsions is supplied, for example, under the name Microfluidizer by Microfluidics.

In order to obtain an emulsion with droplet sizes within the preferred range, whose droplets preferably have a spherical morphology, it may be advantageous when adding the coemulsifiers not to add the coemulsifier or the coemulsifiers until after a preliminary emulsion V1 has been prepared in a component step a1). This preliminary emulsion V1 can be obtained, for example, by emulsifying a mixture of silicone (meth)acrylate of the formula (I), water and emulsifier, preferably particulate emulsifier and more preferably nanoparticulate SiO$_2$ and most preferably LUDOX® SM-AS from Grace Davison, with application of high shear forces, as is possible, for example, with a rotor-rotor system. A suitable rotor-rotor system is supplied, for example, as a Co-Twister homogenizer by Symex.

In the preparation of the preliminary emulsion V2, the coemulsifier is added to the preliminary emulsion V1 in step a2). The coemulsifiers can be added as a pure substance or in the form of a solution, for example of an aqueous solution. The addition of the coemulsifier to the preliminary emulsion V1 allows the droplet size of the drops present in the preliminary emulsion V1 to be effectively frozen. The time of addition of the cosurfactant thus allows the droplet size distribution to be established. Among other parameters, the amount of emulsifier and coemulsifier added can be used to preset the droplet size distribution of the emulsion. The weight ratio of particulate emulsifier to coemulsifiers is preferably 100:1 to 1:1, preferably 50:1 to 3:1.

The preliminary emulsion V2 obtained in step a2) is subsequently dispersed in a homogenizer with interaction chamber in step a3). The emulsion is preferably prepared in step a) by passing the mixture comprising an organic and aqueous phase through and dispersing the mixture in at least one interaction chamber, preferably with a capillary thickness (internal diameter) of 50 to 500 µm, and preferably at a pressure of 50 to 1000 bar, preferably 100 to 800 bar, more preferably 200 to 600 bar, and then decompressing the mixture to ambient pressure, for example into an outlet reservoir. In the course of this, one of the abovementioned preferred droplet sizes is preferably established. It may be advantageous when two or more interaction chambers connected in series are used. In this way, the desired droplet size can be established in a particularly simple manner. One example of a suitable homogenizer is that supplied under the name Microfluidizer by Microfluidics.

In step a3) of the process according to the invention, preference is given to using interaction chambers of which at least one has a capillary thickness of 100 to 300 µm. Particular preference is given to using, in step a) of the process according to the invention, interaction chambers of which at least one has, preferably all have, at least one deflecting bend.

By virtue of the performance of component steps a1) to a3) and the use of the homogenizer with an interaction chamber in component step a3), it is possible in a particularly simple manner to prepare spherical droplets with a desired particle size distribution.

The polymerization in step b) is initiated by the free-radical initiator or initiator system added to the water phase. Process step b) may take place at elevated temperature, but is preferably carried out at room temperature. Preference is given to performing process step b) with stirring. Otherwise, the polymerization in step b) can be carried out in a conventional manner as described in the prior art.

The free-radical initiators used may be customary compounds suitable as free-radical initiators. Possible free-radical initiators may, for example, be peroxodisulphates, for example ammonium or potassium peroxodisulphate, hydrogen peroxide, alkyl hydroperoxides such as t-butyl hydroperoxide, or ammonium or potassium peroxodiphosphate. In these cases, the initiation can be effected, for example, by increasing the temperature. The free-radical initiators used may preferably also be redox systems which also work at low temperatures, preferably at temperatures of less than 70° C., preferably less than 45° C. and more preferably less than 30° C., if appropriate in combination with heavy metal salts having catalytic decomposing action, for example copper or iron salts. Preferred redox systems used as free-radial initiators may, for example, be peroxodisulphates such as ammonium or potassium peroxodisulphate, peroxodiphosphates such as ammonium or potassium peroxodiphosphate, hydrogen peroxide or alkyl hydroperoxide such as t-butyl hydroperoxide, in combination with at least one reducing agent, for example alkali metal hydrogensulphites such as sodium hydrogensulphite, alkali metal dithionites such as sodium dithionite, sodium formaldehydesulphoxylate, or else ascorbic acid. In some cases, it may be advantageous when the free-radical initiators are used in combination with free-radical transferrers. Preferred free-radical transferrers may, for example, be acetylacetone, acetone or the like. Such systems are well known as free-radical initiators and are prior art in the field of emulsion polymerization. In addition, it is possible to add buffer systems to such free-radical initiators, especially those based on a redox system, in order to absorb pH changes as a result, for example, of formation of acidic groups, for example hydrogensulphate groups. Such buffer systems, for example carbonate or phosphate buffers, have likewise been known for a long time and are prior art. Preference is given to using phosphate buffers; particular preference is given to buffers which stabilize the pH in the range around pH 7, for example dialkali metal hydrogenphosphate, especially dipotassium hydrogenphosphate, in the case of formation of acidic groups, for example of hydrogensulphate, or the combination of dialkali metal hydrogenphosphate such as dipotassium hydrogenphosphate, and alkali metal dihydrogenphosphate such as potassium dihydrogenphosphate.

After the performance of polymerization step b), it may be advantageous to remove the resulting particles from the suspension. To this end, for example, the water can be removed by customary methods, for example by filtration or centrifugation. In order to accelerate the drying operation, it may be advantageous to wash the particles, for example with ethanol.

It may be advantageous when the particles are surface-modified after the synthesis. The surface modification can be effected by customary methods known to those skilled in the art. When the particles are core-shell particles and the shell comprises semimetal/metal oxides, especially $SiO_2$, the surface can be modified by processes known to those skilled in the art, for example with trimethylchlorosilane, dimethyldichlorosilane or hexamethyldisilazane or further functional silanes, including alpha-functional silanes, carboxylic acids, etc., in order to obtain functional particles. It is likewise possible to cover the surface with inorganic compounds and elements, for example with silver. In this way, microbicidal particles are obtained.

It may be particularly advantageous when the modifying agent has at least one functional group which can enter into a covalent, ionic or coordinate bond or hydrogen bonds with the surface to be modified. These functional groups may, for example, be carboxylic acid groups, acid chloride groups, ester groups, nitrile and isonitrile groups, OH groups, SH groups, epoxy groups, anhydride groups, acid amide groups, primary, secondary and tertiary amino groups, Si—OH groups, hydrolysable silane radicals (Si—OR) or CH-acidic moieties, as, for example, in beta-dicarbonyl compounds, for example acetylacetone, 2,4-hexanedione, 3,5-heptanedione, diacetyl or acetoacetic acid. It is likewise possible for more than one group of this type to be present in the modifying agent, as, for example, in betaines, amino acids, for example glycine, alanine, beta-alanine, valine, leucine, isoleucine, arginine and aminocaproic acid, and also in EDTA. Carboxylic acids for surface modification are, for example, fatty acids, formic acid, acetic acid, propionic acid, butyric acid, pentanoic acids, hexanoic acid, acrylic acid, adipic acid, succinic acid, fumaric acid, itaconic acid, stearic acid, hydroxystearic acid, ricinoleic acid and polyethercarboxylic acids, and the corresponding anhydrides, chlorides, esters and amides thereof for example methoxyacetic acid, 3,6-dioxaheptanoic acid and 3,6,9-trioxadecanoic acid, and the corresponding acid chlorides, esters and amides.

In addition to the at least one functional group which can enter into a bond with the surface of the core-shell silicone particle, the modifying agent may additionally have further radicals which modify the properties of the particle. Such radicals, or else parts thereof may, for example, be hydrophobic or hydrophilic or bear one or more functional groups in order, in this way, to make the silicone particles compatible with the surrounding medium, to inertize them or to make them reactive, which also includes attachment to the surrounding matrix. These functional groups may, for example, be selected from the range of the alkyl, aryl, alkaryl, aralkyl, fluoroalkyl, hydroxy, alkoxy, polyalkoxy, epoxy, acryloyloxy, methacryloyloxy, acrylate, methacrylate, carboxyl, amino, sulphonyl, sulphate, phosphate, polyphosphate, phosphonate, amide, sulphide, hydrogensulphide, haloalkyl, haloaryl and acyl groups.

When the surface modification is performed with silanes, it may be preferable to use hydrolysable organosilanes which additionally have at least one unhydrolysable radical. Such silanes are represented by the general formula (III)

where
R=identical or different unhydrolysable groups,
X=identical or different hydrolysable groups or hydroxyl groups and
n=1, 2, 3 or 4.

In the general formula (III), the hydrolysable X groups may, for example, be H, halogen (F, Cl, Br, I), alkoxy (preferably methoxy, ethoxy, i-propoxy, n-propoxy or butoxy), aryloxy (preferably phenoxy), acyloxy (preferably acetoxy or propionyloxy), acyl (preferably acetyl), amino, monoalkylamino or dialkylamino groups. In addition, in the general formula (III), the unhydrolysable R radicals may be radicals either with or without functional groups. For instance, R in general formula (III) without functional groups may, for example, be an alkyl, alkenyl, alkynyl, aryl, alkylaryl or aralkyl radical. The R and X radicals may optionally have one or more customary substituents, for example halogen or alkoxy. In radicals of the general formula (III) with a functional group, the functional group may, for example, be selected from the range of the epoxide (e.g. glycidyl or glycidyloxy), hydroxyl, ether, amino, monoalkylamino, dialkylamino, optionally substituted anilino, amide, carboxyl, acryloyl, methacryloyl, acryloyloxy, methacryloyloxy, mercapto, cyano, alkoxy, isocyanato, aldehyde, alkylcarbonyl, acid anhydride, phosphate and polyphosphate groups. These functional groups may be bonded to the silicon atom via alkylene, alkenylene or arylene bridging groups which may be interrupted by oxygen or NH groups. These divalent bridging groups and any substituents present, as in alkylamino groups, may be derived from the corresponding monovalent alkyl, alkenyl, aryl, aralkyl and alkaryl radicals. Of course, the R radical may also have more than one functional group. Unhydrolysable R radicals according to general formula (III) with functional groups may be selected from the range of the glycidyl- or glycidyloxyalkylene radicals, for example β-glycidyloxyethyl, γ-glycidyl-oxypropyl, δ-glycidyloxypropyl, ε-glycidyloxypentyl, ω-glycidyloxyhexyl or 2-(3,4-epoxycyclohexyl)ethyl, the methacryloyloxyalkylene and acryloyloxyalkylene radicals, for example methacryloyloxymethyl, acryloyloxymethyl, methacryloyloxyethyl, acryloyloxyethyl, methacryloyloxypropyl, acryloyloxypropyl, methacryloyloxybutyl or acryloyloxybutyl, and the 3-isocyanatopropyl radical.

In addition, it is also possible to use silanes with at least partly fluorinated alkyl radicals, for example 3,3,4,4,5,5,6,6,7,7,8,8,8-tridecafluorooctyl or 3,3,3-trifluoropropyl groups.

When the shell of the silicone (meth)acrylate particles is formed from SiO$_2$, it bears a negative charge in the alkaline, neutral and also weakly acidic pH range, since the solid-state stabilizer particles have a negative ζ potential there. This allows modification with cationic substances or cationic polymers, which can be conducted up to a charge reversal of the particles. Examples of such cationic substances may be polydimethyldiallylammonium chloride (PDADMAC), chitosan, quaternized cellulose derivatives (for example Polyquaternium-10), quaternary (organo)polysiloxanes (for example Quaternium-80, for example ABIL® Quat 3272 or ABIL® Quat 3474 from Evonik Goldschmidt GmbH), or else modified polyurea structures, as in Ralumer 11 from Raschig. Such a modification allows, for example, adhesion of the particles thus modified to negatively charged surfaces, as can be found in many textile fibres, skin or hair.

It is likewise possible, especially in the case of oxidic particles, for example colloidal silica, as obtainable, for example, from Grace Davison as LUDOX®, to perform a surface modification with siloxanes and organopolysiloxanes. This can be done by the use of dimethylpolysiloxanes end-capped with trimethylsiloxy groups, cyclic dimethylpolysiloxanes, α,ω-dihydroxypolydimethylsiloxanes, cyclic methylphenylsiloxanes, methylphenylpolysiloxanes end-capped with trimethylsiloxy groups, or of dimethylsiloxane-methylphenylsiloxane copolymers end-capped with trimethylsiloxy groups, optionally in the presence of a suitable catalyst (for example ammonium carbamate or alkali metal hydroxides) and optionally also elevated temperatures.

The surface modification with polysiloxanes or organopolysiloxanes can be effected covalently or else adsorptively; examples of such substance classes are organopolysiloxanes modified terminally and/or in comb positions with polyether or polyester chains. It is equally possible to use monofunctional polysiloxanes for surface modification of the particles, for example α-halo-, α-alkoxy- and α-hydroxydimethylpolysiloxanes end-capped with trimethylsilyl groups.

The inventive silicone (meth)acrylate particles are notable in that they are obtainable by the process according to the invention and thus comprise a polymer which has been obtained by polymerizing siloxane (meth)acrylate(s) of formula (I) and optionally other monomers, optionally in the presence of further components, for example fillers, assistants or active substances, etc., in the presence of a free-radical initiator, especially of a redox system as a free-radical initiator. Preferred inventive silicone (meth)acrylate particles are those which possess a core-shell structure (so-called silicone (meth)acrylate composite particles). In these, a shell, which is preferably formed by particulate emulsifiers, surrounds the inner core, which comprises the polymerized silicone (meth)acrylate. Particularly preferred silicone (meth)acrylate particles are those in which the shell is formed from the above-mentioned inorganic particles whose surface is preferably modified.

Preferred silicone (meth)acrylate composite particles may be those in which the shell is modified. Such a modification can be effected, for example, with cationic substances such as organic ammonium ions or cationic polymers, cationic siloxanes, organic polymers, for example polyacrylates, carboxylic acids or carboxylic acid anions, chelating agents, diketones, siloxanes or condensed silanes as described above. The surface modification may be bonded physically or chemically to the polymer particle. In addition, the surface modifiers may bear functional groups, as, for example, in the case of use of functional silanes. The surface modifiers may consist of discrete molecules, or else be crosslinked.

In addition to the silicone (meth)acrylate, the particles may comprise components formed from comonomers which may have been used in the polymerization. These comonomers may have reacted to be fully or partly incorporated into the polysiloxane (meth)acrylate network or else be present as a separate network. Mixed forms of these described limiting cases are equally possibly and form part of this invention.

It may be advantageous when the particles comprise further components which are not constituents which have originated from the emulsifiers, monomers or comonomers. Such components may be functional components, for example UV stabilizer pigments, or nonfunctional components, for example fillers. The content of such further components may be 0.01 to 99% by weight, preferably 0.1 to 80% by weight and more preferably 1 to 50% by weight, based on the content of silicone meth(acrylate). The further components may be added subsequently to the already polymerized particles through swelling and diffusion. This can also proceed with the aid of a solvent which is removed again thereafter. However, it is also possible to add the further components in the course of the preparation process (see above). In particular, the further components can be added to the organic phase in step a) of the process according to the invention. The further components may be present dissolved in the polymer matrix or else attached to the matrix through a possibly labile covalent bond.

The further components which may be present in the inventive particles may, for example, be dyes, odorants, plasticizers, pheromones, hormones, growth substances, cosmetic oils and active ingredients, disinfectants, active antimicrobial ingredients, UV absorbers, antioxidants, biocides, preservatives, active pharmaceutical ingredients and many others.

The further components present in the inventive particles may especially be linear or branched dimethylpolysiloxanes end-capped with trimethylsiloxy groups, cyclic dimethylpolysiloxanes, cyclic methylphenylsiloxanes, methylphenysiloxanes end-capped with trimethylsiloxy groups, dimethylsiloxane-methylphenylsiloxane copolymers end-capped with trimethylsiloxy groups, dimethylsiloxane-methylfluoroalkylsiloxane copolymers end-capped with trimethylsiloxy groups where the fluoroalkyl radical is, for example, a 3,3,4,4,5,5,6,6,7,7,8,8,8-tridecafluorooctyl or a 3,3,3-trifluoropropyl group, $\alpha,\omega$-dihydroxypolydimethylsiloxanes, polydimethylsiloxanes alkoxylated in the terminal and/or comb positions, polydimethylsiloxanes alkylated in the terminal and/or comb positions, and mixed forms composed of polydimethylsiloxanes alkylated and alkoxylated in the terminal and/or comb positions, quaternary (organo)polysiloxanes such as ABIL® Quat 3272 and ABIL® Quat 3474 (also known as Quaternium-80), alkanes, for example hexane and higher homologues or cycloalkanes and higher homologues, and also liquid paraffins and isoparaffins, squalane, aromatic hydrocarbons, for example benzene or toluene, halogenated hydrocarbons, for example carbon tetrachloride or methylene chloride, ketones, for example acetone, diethyl ketone or methyl isobutyl ketone, alcohols, for example undecyl alcohol, stearyl alcohol, cetylstearyl alcohol, oleyl alcohol, ethers, for example dibutyl ether, esters, for example bis(2-ethylhexyl) carbonate, isononyl isononanoate, isopropyl laurate, isopropyl palmitate, hexyl laurate, isopropyl myristate, myristyl myristate, cetyl myristate, 2-octyldecyl myristate, isopropyl palmitate, 2-ethylhexyl palmitate, butyl stearate, decyl oleate, 2-octyldodecyl oleate, myristyl lactate, cetyl lactate, lanolin acetate, natural or nature-identical oils, for example avocado oil, almond oil, olive oil, cocoa oil, jojoba oil, sesame oil, sunflower oil, soya oil, camellia oil, cedar oil, apricot kernel oil, castor oil, mink oil, groundhog grease, cottonseed oil, coconut oil, egg oil, pork fat, glycol esters, for example polypropylene glycol monooleate or neopentyl glycol 2-ethylhexanoate, glyceryl esters, for example glyceryl triisostearate or glyceryl esters of coconut fatty acid, and alkoxylated fatty alcohols, for example lauryl alcohol ethoxylates or cetyl alcohol propoxylates, terpene alcohols, for example citronellol, menthol, linalool, farnesol, nerolidol, nerol, geraniol, borneol, ipsenol, bisabolol or terpineol, terpenes, for example menthane, terpinene, phellandrene, pinene or limonene, terpene aldehydes, for example citral, terpene ketones, for example menthone, pulegone or carvone, terpene derivates, for example camphor, diterpenes, for example retinol, phenolic substances, for example thymol, eugenol, tocopherol or vanillin, pheromones, for example verbenone, cholesterol derivatives, for example testosterone, androsterone, oestradiol or cortisone, antibiotics, for example metronidazole or dexamethasone, fungicides, for example orthophenylphenol or thiabendazole, antimycotics, for example ketoconazole or tolnaftate, and many others.

Particularly preferred further components for cosmetic applications are tocopherol, tocopherol acetate, tocopherol palmitate, ascorbic acid, ascorbyl palmitate, deoxyribonucleic acid, coenzyme Q10, retinol and retinyl derivates, bisabolol, allantoin, phytantriol, panthenol, AHA acids, amino acids, hyaluronic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolysates, plant extracts and vitamin complexes. It is also possible for dehydroxyacetone and organic sunscreen filters to be present as further components. The aforementioned further components may be present especially as functional components in the inventive particles. When the functional components are free-radical scavengers, such functional components are not added to the particles until after completion of the free-radical polymerization step b). This can be done, for example, through swelling/diffusion.

The inventive silicone meth(acrylate) particles may include one or more substances, especially selected from the abovementioned further components, which can be released from the particles. The release may proceed over a prolonged period in the appropriate applications. The release may proceed, for example, through diffusion or hydrolysis reactions and subsequent diffusion.

The substances to be released which may be present in the particles are, for example, cosmetic oils and active ingredients, fragrances, active pharmaceutical ingredients, including, for example, silver and silver compounds, and also dyes and preservatives. These substances may be present in dissolved form or embedded in the silicone (meth)acrylate matrix or bonded to the silicone (meth)acrylate matrix by a labile chemical bond. The substances to be released may especially be the abovementioned further components.

The inventive silicone meth(acrylate) particles or those prepared in accordance with the invention may be used alone or in a mixture with further particles, pigments and/or further customary additives in the form of powders or dispersions in coating, adhesive or sealant materials, in polymers, in defoamers, in wetting and levelling aids, in cosmetic or pharmaceutical formulations and care products, in cleaning and detergent compositions or in applications for modifying the interface properties of solid and liquid substrates, for example the tactile properties, hydrophobization or modification of lubricant and/or release properties.

The inventive compositions comprise the inventive silicone (meth)acrylate particles or those prepared in accordance with the invention. Such inventive compositions may, for example, be dispersions of silicone (meth)acrylate composite particles in aqueous or organic media, in which case a dispersing aid, a surfactant and/or a thickener may optionally be added to the dispersion.

To prepare such dispersions, the particles prepared in accordance with the invention are dispersed in a medium, for example water, alcohols, aliphatic or aromatic hydrocarbons and silicones. The particles may be stabilized in the surrounding medium by electrostatic means, for example via the pH, by steric means, for example by means of dispersing additives or emulsifiers, or else by electrosteric means. It is possible to use anionic, cationic, amphoteric or nonionic surfactants or mixtures of the aforementioned substance classes in the preparation of the dispersions. Cationic surface-active components may, for example, be selected from salts of primary, secondary or tertiary amines, alkyltrimethylammonium salts, dialkyldimethylammonium salts, trialkylmethylammonium salts, tetraalkylammonium salts, alkoxylated alkylammonium salts, alkylpyridinium salts or N,N-dialkylmorpholinium salts. Anionic surface-active compounds may, for example, be selected from salts of aliphatic carboxylic acids, alkylbenzenesulphonates, alkylnaphthylsulphonates, alkylsulphonates, dialkyl sulphosuccinates, α-olefinsulphonates, salts of α-sulphonated aliphatic carboxylic acids, N-acyl-N-methyltaurates, allyl sulphates, sulphated oils, polyethoxylated alkyl ether sulphates, polyethoxylated alkylphenyl ether sulphates, alkyl phosphates, polyethoxylated alkyl ether sulphates, polyethoxylated alkylphenyl ether sulphates, and condensates of formaldehyde and naphthylsulphonates. Amphoteric surface-active compounds may, for example, be selected from N,N-dimethyl-N-alkyl-N-carboxymethylammonium betaines, N,N-dialkylaminoalkylenecarboxylates, N,N,N-trialkyl-N-sulphoalkyleneammonium betaines, N,N-dialkyl-N,N-bispolyoxyethyleneammonium sulphate ester betaines, 2-alkyl-1-carboxymethyl-1-hydroxyethylimidazolinium betaines.

Nonionic surface-active compounds may, for example, be selected from polyethoxylated alkyl ethers, polyethoxylated alkenyl ethers, polyethoxylated alkylphenyl ethers, polyethoxylated polystyrene phenyl ethers, polyoxyethylene-polyoxypropylene glycols, polyoxyethylene-polyoxypropylene alkyl ethers, partial esters of aliphatic carboxylic acids with polyfunctional alcohols, for example sorbitan esters, aliphatic glyceryl esters, aliphatic polyglyceryl esters, aliphatic decaglycerol ester, (mixed) aliphatic esters of ethylene glycol/pentaerythritol, (mixed) aliphatic esters of propylene glycol/pentaerythritol, polyethoxylated aliphatic partial esters of polyfunctional alcohols, for example polyethoxylated aliphatic sorbitan partial esters, ethoxylated aliphatic glyceryl esters, mixed ethoxylated/aliphatically esterified acids, aliphatic carboxylic esters of polyglyercols, polyethoxylated castor oil, diethanolamides of aliphatic carboxylic acids, polyethoxylated alkylamines, aliphatic partial esters of triethanolamine, trialkylamine oxides, and polyalkoxylated organopolysiloxanes. Such dispersing additives may, for example, be selected from the product portfolio of Evonik Goldschmidt GmbH, which are obtainable there, for example, under the names "Tego® Dispers" or "Tegopren®". The content of such surface-active substances may be between 0.1 and 50% by weight, preferably between 1 and 30% by weight, based on the dispersion. The content of dispersed particles in the dispersion is preferably 0.1 to 80% by weight, preferably 1 to 40% by weight.

To stabilize and establish the desired viscosity, it is also possible to add further substances to the dispersion. Examples include solvents miscible with the dispersion medium or else soluble polymers, for example xanthan gum, guar flour, carboxymethylcellulose, polyvinyl alcohol, polyvinylpyrrolidone, carboxyvinyl polymers, polyacrylates, hydroxyethylcellulose, polyethylenimines, polyethoxylated glycol stearate, and also clays, sheet silicates, pyrogenic oxides such as AEROSIL® (Evonik Degussa GmbH), hydroxy fatty acid glycerides, hydroxy fatty acids, aluminium tristearate, polyolefin waxes and amide waxes.

It is equally possible to add further functional substances to the dispersions, examples including film-forming poly(meth)acrylates, silicone/(meth)acrylate copolymers, poly-N-acylalkyleneimines, poly-N-methylpyrrolidones, silicone resins, with fluorinated organic groups, amino or silanol groups, antioxidants, for example BHA, BHT, ascorbic acid and γ-oryzanol, antifreezes, for example ethanol, ethylene glycol, 1,3-butylene glycol, propylene glycol, glycerol or isopropanol, antimicrobial substances and preservatives such as triclosan and triclocarban and hexachlorophene, complexing agents, for example EDTA (acid and salts), citric acid and etidronic acid and salts thereof, UV absorbers, for example derivatives of benzophenone, of benzotriazole, cinnamic esters, or particulate UV absorbers, for example ZnO or $TiO_2$, dye and colorants, pigments, spraying aids, wetting agents, vitamins, growth substances, hormones and fragrances.

The dispersions comprising the inventive particles can be prepared by means of customary methods according to the prior art, but it is advantageous to further process the particles formed after the polymerization in step b) of the process according to the invention and wash with alcohol(s) or water, without preceding drying, to aqueous dispersions, for example. This is also possible when, for example, a desired surface modification can be effected directly from aqueous or alcoholic phase, which has a favorable effect on the process economics.

The inventive silicone (meth)acrylate particles or dispersions comprising them may find use as additives in cosmetics and toiletries, for example as a matting agent, as an absorber for sebum or for generating a silky skinfeel, as additives for improving the mechanical properties of polymers and lacquers or coatings, for example for increasing abrasion or scratch resistance, flexibility and also impact resistance, and additionally as an antiblocking agent for improving the sliding properties of a wide variety of different surfaces, as flow or dispersing aid in powders, as additives in toners, as a mild abrasive in washing and care formulations, and as formulation constituents or carrier materials which release active ingredients or assistants over a prolonged period.

The inventive compositions may especially also be a coating, adhesive or sealant material, a polymer, a defoamer, wetting and/or levelling aid, a cosmetic, a care product, a medical product, a pharmaceutical, a washing composition, a cleaning and/or detergent composition, a hydrophobizing agent, a lubricant or a release agent.

The following examples are provided for illustrative purposes only.

Example 1

Particles of TEGO® RC 726 Silicone Acrylate 7600 g of demineralized water and 276 g of Ludox SM-AS were mixed and adjusted to pH 7 with hydrochloric acid. The mixture was initially charged in a stirred tank of a Co-Twister homogenizer (Symex), and 2156 g of TEGO® RC 726 (Evonik Goldschmidt GmbH) were added with stirring. After the tank had been closed, with gentle stirring, the tank was evacuated to 50 mbar and, after the evolution of foam had abated, vented back to 800 mbar. The mixture was subsequently pre-emulsified at a rotor speed of 2000 rpm and a differential speed of 20 m/s for 15 min in the system cycle. After 64.3 g of a 5% by weight aqueous CTAB (cetyltrimethylammonium bromide) solution and then 420 g of demineralized water had been sucked in, the mixture was emulsified under the same conditions for an additional 45 minutes. The resulting preliminary emulsion was homogenized by passing through a homogenizer (in the examples, a Microfluidizer from Microfluidics was used in each case) with an interaction chamber of diameter 200 µm at pressure 800 bar.

For the polymerization, 850 g of the emulsion were admixed in a 2 l round-bottom flask with a solution of 6.8 g of ammonium peroxodisulphate in 20 ml of demineralized water. Thereafter, a nitrogen stream was introduced with stirring for 45 min. Subsequently, a solution of 27.2 g of disodium hydrogenphosphate in 100 ml of demineralized water and 4.25 g of an aqueous 38% by weight sodium hydrogensulphite solution were added under nitrogen. The reaction mixture was stirred for a further 2 h and then left to stand overnight. The resulting particles were filtered off with suction, washed by slurrying with water and ethanol and dried to constant mass in a vacuum drying cabinet at 50° C.

Example 2

Particles of TEGO® RC 902 Silicon Acrylate 4650 g of demineralized water and 160 g of Ludox SM-AS were mixed and adjusted to pH 7 with hydrochloric acid. The mixture was initially charged in a stirred tank of a Co-Twister homogenizer (Symex), and 1250 g of TEGO® RC 902 (Evonik Goldschmidt GmbH) were added with stirring. After the tank had been closed, with gentle stirring, the tank was evacuated to 50 mbar and, after the evolution of foam had abated, vented back to 800 mbar. The mixture was subsequently pre-emulsified at a rotor speed of 2000 rpm and a differential speed of 20 m/s for 15 min in the system cycle. After 37.3 g of a 5% by weight aqueous CTAB (cetyltrimethylammonium bromide) solution and then 245 g of demineralized water had been sucked in, the mixture was emulsified under the same conditions for an additional 45 minutes. The resulting preliminary emulsion was homogenized by passing through a homogenizer with an interaction chamber of diameter 200 µm at pressure 800 bar.

For the polymerization, 850 g of the emulsion were admixed in a 2 l round-bottom flask with a solution of 6.8 g of ammonium peroxodisulphate in 20 ml of demineralized water. Thereafter, a vigorous nitrogen stream was introduced with stirring for 45 min. Subsequently, a solution of 27.2 g of disodium hydrogenphosphate in 100 ml of demineralized water and 4.25 g of an aqueous 38% by weight sodium hydrogensulphite solution were added under nitrogen. The reaction mixture was stirred for a further 2 h and then left to stand overnight. The resulting particles were filtered off with suction, washed by slung with water and ethanol and dried to constant mass in a vacuum drying cabinet at 50° C.

Example 3

Particles of TEGO® RC 2015 Silicone Acrylate 4000 g of demineralized water and 800 g of Ludox SM-AS were mixed and adjusted to pH 7 with hydrochloric acid. The mixture was initially charged together with 18 600 g of demineralized water in a stirred tank of a Co-Twister homogenizer (Symex), and 6250 g of TEGO® RC 2015 (Evonik Goldschmidt GmbH) were added with stirring. After the tank had been closed, with gentle stirring, the tank was evacuated to 50 mbar and, after the evolution of foam had abated, vented back to 600 mbar. The mixture was subsequently pre-emulsified at a rotor speed of 3500 rpm and a differential speed of 40 m/s for 45 min. After 157.5 g of a 5% by weight aqueous CTAB (cetyltrimethylammonium bromide) solution and then 400 g of demineralized water had been sucked in, the mixture was emulsified under the same conditions for an additional 45 minutes. Before the mixture was discharged, it was deaerated at 200 mbar and a rotor speed of 2000 rpm with co-rotatory rotors. The resulting preliminary emulsion was homogenized by passing through a homogenizer with an interaction chamber of diameter 200 µm at pressure 600 bar.

For the polymerization, 850 g of the emulsion were admixed in a 2 l round-bottom flask with a solution of 6.8 g of ammonium peroxodisulphate in 20 ml of demineralized water. Thereafter, a vigorous nitrogen stream was introduced with stirring for 45 min. Subsequently, a solution of 27.2 g of disodium hydrogenphosphate in 100 ml of demineralized water and 4.25 g of an aqueous 38% by weight sodium hydrogensulphite solution were added under nitrogen. The reaction mixture was stirred for a further 2 h and then left to stand overnight. The resulting particles were filtered off with suction, washed by slurrying with water and ethanol and dried to constant mass in a vacuum drying cabinet at 50° C.

Example 4

Particles of a Mixture of TEGO® RC 726 and TEGO® RC 902 Silicone Acrylates 186 g of demineralized water were mixed with 12.8 g of Ludox SM-AS and adjusted to pH 7 with dilute Hcl. 25 g of RC726 and 25 g of TEGO® RC 902 (Evonik Goldschmidt GmbH) were mixed to give a solution and pre-emulsified with the aqueous phase in a vacuum dissolver with a mizer disc at 4000 rpm for 15 minutes. Subsequently, 2.5 g of a 5% by weight aqueous CTAB solution were added and the mixture was emulsified at 4000 rpm in the vacuum dissolver for an additional 30 minutes.

The resulting preliminary emulsion was homogenized by passing it through a homogenizer with an interaction chamber with a microchannel of diameter 200 µm at pressure 800 bar.

For the polymerization, 100 g of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying with water and ethanol and dried to constant mass in a vacuum drying cabinet at 50° C.

Example 5

Particles of TEGO® RC 726 Silicone Acrylate and Methyl Methacrylate (MMA)

188 g of demineralized water were mixed with 12.6 g of Ludox SM-AS and adjusted to pH 7 with dilute hydrochloric acid. To this was added a solution of 45 g of TEGO® RC726 (Evonik Goldschmidt GmbH) and 5 g of MMA, which were pre-emulsified in a vacuum dissolver with a mizer disc at 4000 rpm for 15 min. Subsequently, 2.6 g of a 5% by weight aqueous CTAB solution were added and the mixture was emulsified at 4000 rpm in the vacuum dissolver for an additional 30 minutes.

The resulting preliminary emulsion was homogenized by passing it through a homogenizer with an interaction chamber with a microchannel of diameter 200 µm at pressure 800 bar.

For the polymerization, 100 ml of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying with water and ethanol and dried to constant mass in a vacuum drying cabinet at 50° C.

Example 6

Particles of TEGO® RC 726 Silicone Acrylate Filled with AEROSIL® R 974

10 g of AEROSIL® R974 (Evonik Degussa GmbH) were dispersed in a vacuum dissolver into 90 g of TEGO® RC 726 (Evonik Goldschmidt GmbH) at 4000 rpm for 10 min. 186 g of demineralized water were mixed with 12.8 g of Ludox SM-AS and adjusted to pH 7 with dilute HCl. To this were added 50 g of the prepared dispersion of AEROSIL® R 974 in TEGO® RC 726 silicone acrylate, which were pre-emulsified in a vacuum dissolver with a mizer disc at 4000 rpm for 15 min. Subsequently, 2.6 g of a 5% by weight aqueous CTAB solution were added and the mixture was emulsified in the vacuum dissolver at 4000 rpm for an additional 30 minutes.

The resulting preliminary emulsion was homogenized by passing it through a homogenizer with an interaction chamber with a microchannel of diameter 200 μm at pressure 800 bar.

For the polymerization, 100 ml of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying with water and ethanol and dried to constant mass in a vacuum drying cabinet at 50° C.

Example 7

Particles of TEGO® RC 726 Silicone Acrylate Comprising Menthol 90 g of TEGO® RC 726 silicone acrylate (Evonik Goldschmidt GmbH) were mixed with a solution of 10 g of menthol in 20 g of acetone, and the acetone was drawn off under reduced pressure. 186 g of demineralized water were mixed with 12.8 g of Ludox SM-AS and adjusted to pH 7 with dilute HCl. To this were added 50 g of the menthol solution, which were pre-emulsified in a vacuum dissolver with a mizer disc at 4000 rpm for 15 min. Subsequently, 2.6 g of a 5% by weight aqueous CTAB solution were added and the mixture was emulsified in the vacuum dissolver at 4000 rpm for an additional 30 minutes. The resulting preliminary emulsion was homogenized by passing it through a homogenizer with an interaction chamber with a microchannel of diameter 200 μm at pressure 800 bar.

For the polymerization, 100 ml of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying twice with water and dried at room temperature. The particles thus obtained had a distinct menthol odour.

Example 8

Particles of TEGO® RC 726 Silicone Acrylate and ABIL® Quat 3474

98 g of TEGO® RC 726 silicone acrylate (Evonik Goldschmidt GmbH) were mixed with 2 g of ABIL® Quat 3474 (diquaternary polydimethylsiloxane, Evonik Goldschmidt GmbH). 186 g of demineralized water were mixed with 12.8 g of Ludox SM-AS and adjusted to pH 7 with dilute HCl. To this were added 50 g of the prepared solution of ABIL® Quat 3474 in TEGO® RC 726, which were pre-emulsified in a vacuum dissolver with a mizer disc at 4000 rpm for 15 min. Subsequently, 2.6 g of a 5% by weight aqueous CTAB solution were added and the mixture was emulsified in the vacuum dissolver at 4000 rpm for an additional 30 minutes.

The resulting preliminary emulsion was homogenized by passing it through a homogenizer with an interaction chamber with a microchannel of diameter 200 μm at pressure 800 bar.

For the polymerization, 100 ml of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying with water and ethanol and dried in a vacuum drying cabinet at 50° C.

Example 9

Particles of TEGO® RC 902 Silicone Acrylate Comprising Cyclomethicone

Mixture of Octamethylcyclotetrasiloxane and Decamethylcyclotetrasiloxane 45 g of TEGO® RC 902 silicone acrylate (Evonik Goldschmidt GmbH) were mixed with 5 g of cyclomethicone. 186 g of demineralized water were mixed with 3.2 g of Ludox® SM-AS and adjusted to pH 7 with dilute HCl. To this was added the above-prepared solution of cyclomethicone in TEGO® RC 902, which was pre-emulsified in a vacuum dissolver with a mizer disc at 4000 rpm for 15 min. Subsequently, 0.65 g of a 5% by weight aqueous CTAB solution was added and the mixture was emulsified in the vacuum dissolver at 4000 rpm for an additional 30 minutes.

The resulting preliminary emulsion was homogenized by passing it through a homogenizer with an interaction chamber with a microchannel of diameter 200 μm at pressure 800 bar.

For the polymerization, 100 ml of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying twice with water and dried at room temperature.

Example 10

Particles of TEGO® RC 902 Silicone Acrylate Comprising Tegiloxan® 3

45 g of TEGO® RC 902 silicone acrylate (Evonik Goldschmidt GmbH) were mixed with 5 g of Tegiloxan® 3 (silicone oil 3 cSt, Evonik Goldschmidt GmbH). 186 g of demineralized water were mixed with 3.2 g of Ludox® SM-AS and adjusted to pH 7 with dilute HCl. To this was added the above-prepared solution of Tegiloxan®3 in TEGO® RC 902, which was pre-emulsified in a vacuum dissolver with a mizer disc at 4000 rpm for 30 min. Subsequently, 0.65 g of a 5% by weight aqueous CTAB solution was added and the mixture was emulsified in the vacuum dissolver at 4000 rpm for an additional 60 minutes.

The resulting preliminary emulsion was homogenized by passing it through a homogenizer with an interaction chamber with a microchannel of diameter 200 μm at pressure 800 bar.

For the polymerization, 100 ml of the resulting emulsion were admixed with 0.8 g of ammonium peroxodisulphate in 5 ml of demineralized water and purged with a vigorous nitrogen stream with stirring over 30 minutes. Subsequently, a solution of 3.2 g of disodium hydrogenphosphate, 0.5 g of a 38% by weight aqueous sodium hydrogensulphite solution and 30 g of demineralized water were added and the mixture was stirred under nitrogen for a further 2 hours. The resulting dispersion was left to stand overnight. The resulting particles were filtered off with suction, washed by slurrying twice with water and dried at room temperature.

Example 11

Silicone Oil Absorption of Particles of TEGO® RC 902 Silicone Acrylate with Dichloromethane Solvent 10 g of silicone particles from example 2 (TEGO® RC 902 silicone acrylate polymerized) were admixed with a solution of 2.5 g of silicone oil (polydimethylsiloxane, 350 cSt) in 80 g of dichloromethane, and left to swell overnight. Subsequently, the dichloromethane was drawn off slowly under reduced pressure. A pulverulent, nontacky residue was obtained, from which it was impossible to press out any silicone oil onto filter paper (black-band filter) by finger pressure.

Example 12

Silicone Oil Absorption of Silicone Particles of TEGO® RC 726 Silicone Acrylate 10 g of silicone acrylate particles from example 1 were admixed with 30 g of TEGILOXAN® 3 (3 cSt, Evonik Goldschmidt GmbH) and left to stand for 36 h. The residual oil was absorbed from the swollen particles by means of a black-band filter, rinsed with a little ethanol in the filter and dried. 12.8 g of a dry white powder were obtained which released a portion of the liquid absorbed again onto a filter paper when pressed hard.

Example 13

Silicone Oil Absorption of Silicone Particles of TEGO® RC 726 Silicone Acrylate 10 g of silicone acrylate particles from example 1 were admixed with 30 g of cyclomethicone (mixture of octamethylcyclotetrasiloxane and decamethylcyclopentasiloxane) and left to stand for 36 h. The residual oil was absorbed from the swollen particles by means of a black-band filter, rinsed with a little ethanol in the filter and dried. 14.7 g of a dry white powder were obtained which released a portion of the liquid absorbed again onto a filter paper when pressed hard.

Example 14

Surface Modification of Particles of TEGO® RC 726 Silicone Acrylate Comprising 3-methacryloyloxypropyltrimethoxysilane 9.9 g of silicone acrylate particles from example 1 were stirred in 13.1 g of methanol so as to form a paste. To this paste were added 0.5 g of 3-methacryloyloxypropyltrimethoxysilane (Dynasylan® MEMO, Evonik Degussa GmbH) and two drops of formic acid, and the mixture was mixed thoroughly. After standing overnight, the volatile constituents were removed by rotary evaporation at 50° C. in an oil-pump vacuum.

Example 15

Particle Dispersion of TEGO® RC 726 Silicone Acrylate Comprising TEGO® CARE PL 4 and Sodium Laurylsulphate as Emulsifiers In a 5 l beaker, 968 g of demineralized water were admixed with 75 g of TEGO® CARE PL 4 (nonionic emulsifier, Evonik Goldschmidt GmbH) and 7.5 g of sodium laurylsulphate, and homogenized with stirring. 450 g of TEGO® RC 726 were added and the mixture was pre-emulsified with stirring with a mizer disc at 200 rpm for one hour.

The resulting preliminary emulsion was homogenized by passing it through a homogenizer with an interaction chamber of diameter 200 μm at pressure 800 bar.

1340 g of the resulting emulsion were admixed in a 4 l four-neck flask with 33 g of ammonium peroxodisulphate in 50 g of demineralized water, and deaerated with a vigorous nitrogen stream with stirring with a precision glass stirrer for 30 min. A solution of 127 g of disodium hydrogenphosphate dihydrate and 7.1 g of sodium hydrogensulphite solution (38% by weight, aqueous) in 250 g of warm demineralized water was added and the reaction mixture was stirred under nitrogen for an additional hour. After leaving to stand overnight, the reaction mixture was filtered through a 230 μm fast sieve; the filtrate obtained was a silicone acrylate particle dispersion.

Examples 16 to 19, Comparative Examples C1 and C2

Use Examples, Cosmetics

As comparative examples C1 and C2, the corresponding emulsions are prepared without silicone acrylate particles.

Examples 16 and 17 are emulsions of the oil-in-water type; example 18 represents an emulsion of the water-in-oil type.

The pigments used were titanium dioxide in example 19 (sunscreen), while customary iron oxides in combination with titanium dioxide were used in example 18 (foundation). Comparative example C2 serves in particular to document the sensory advantages which are achievable through the use of the inventive particles in pigment-containing formulations.

In example emulsion 16 and in C1 the emulsion was prepared in a hot-hot process (oil and water phases homogenized at 70 to 75° C. by customary methods).

Example emulsion 17 shows that the inventive particles can also be stirred into a cold-preparable emulsion without any problem. In this case, oil and water phases are combined at room temperature and homogenized by customary methods.

Example emulsion 18 was prepared in a cold-cold process at room temperature. In this case, the first of the oil phase was homogenized and then the water phase was added with gentle stirring. After the addition of water had ended, the mixture was homogenized again.

In the case of example emulsion 19, the preparation was effected in a hot-hot process, by combining and homogenizing the oil and water phases heated to 80° C.

Generally, the examples show that the inventive particles can either be added directly to the oil phase (as for instance in example 18) or can be incorporated subsequently into the finished emulsion (as in example 16 or 17).

The compositions of the example formulations and comparative formulations are specified in tables 1 to 4 which follow.

TABLE 1

Formulations and results of example 16 and comparative example C1, oil-in-water care cream:

| Example | 16 | C1 |
|---|---|---|
| A TEGO ® Care 165 (Evonik Goldschmidt GmbH) (Glyceryl stearate; PEG-100 stearate) | 6.0% | 6.0% |
| Stearyl alcohol | 3.0% | 3.0% |
| Mineral oil | 4.0% | 4.0% |
| Ethylhexyl palmitate | 4.0% | 4.0% |
| B Glycerol | 3.0% | 3.0% |
| Water | 75.0% | 80.0% |
| C Silicone acrylate particles from ex. 1 | 5.0% | |
| Z Preservative, perfume | q.a. | q.a. |
| Stability | Good | Good |
| Appearance | White, homogeneous | White, homogeneous |
| Skinfeel | Velvety/silky, smooth; not rough | Waxy, rough |

TABLE 2

Formulation and results of the oil-in-water body care lotion prepared cold in example 17:

| Example | 17 |
|---|---|
| A TEGO ® Care LTP (Evonik Goldschmidt GmbH) (sorbitan laurate; polyglyceryl-4 laurate; dilauryl citrate) | 1.5% |
| Cyclopentasiloxane | 10.0% |
| Isohexadecane | 3.5% |
| Ethylhexyl palmitate | 1.1% |

TABLE 2-continued

Formulation and results of the oil-in-water body care lotion prepared cold in example 17:

| Example | 17 |
|---|---|
| TEGO ® Carbomer 140 (Evonik Degussa GmbH) | 0.15% |
| TEGO ® Carbomer 141 (Evonik Degussa GmbH) | 0.15% |
| Xanthan gum | 0.1% |
| B Glycerol | 3.0% |
| Water | 79.6% |
| C NaOH (10% solution) | 0.90% |
| D Silicons acrylate particles from ex. 1 | 5.0% |
| Z Preservative, perfume | q.a. |
| Stability | Good |
| Appearance | White, homogeneous |
| Skinfeel | Light; velvety; smooth |

TABLE 3

Water-in-oil foundation from example 18 and comparative example C2:

| Example | 18 | C2 |
|---|---|---|
| A ABIL ® EM 90 (Evonik Goldschmidt GmbH) (Cetyl PEG/PPG-10/1 dimethicone) | 3.0% | 3.0% |
| Diethylhexyl carbonate | 10.0% | 10.0% |
| Cyclopentasiloxane | 7.6% | 7.6% |
| Ethylhexyl palmitate | 3.4% | 3.4% |
| Iron oxides | 1.8% | 1.8% |
| Titanium dioxide | 7.2% | 7.2% |
| Talcum | 2.0% | 2.0% |
| Sllicone acrylate particles from ex. 1 | 2.5% | |
| B NaCl | 1.0% | 1.0% |
| Glycerol | 2.0% | 2.0% |
| Water | 65.5% | 68.0% |
| Z Preservative, perfume | q.a. | q.a. |
| Stability | Good | Good |
| Appearance | Homogeneous, brownish | Homogeneous, brownish |
| Skinfeel | Smooth, not rough, velvety | Somewhat dry and rough |

TABLE 4

Oil-in-water sunscreen lotion according to example 19

| Example | 19 |
|---|---|
| A AXOL ® C 62 (Evonik Goldschmidt GmbH) (Glyceryl stearate citrate) | 2.0% |
| Cetearyl alcohol | 1.0% |
| $C_{12-15}$ alkyl benzoate | 8.0% |
| Triisostearin | 1.0% |
| Diethylhexyl carbonate | 2.75% |
| Tocopheryl acetate | 0.5% |
| Xanthan gum | 0.4% |
| Ethylhexyl methoxycinnamate | 7.0% |
| Butyl methoxydibenzoylmethane | 3.0% |
| TEGO ® Sun T 805 (Evonik Goldschmidt GmbH) (Titanium dioxide; trimethoxy-caprylylsilane) | 2.25% |
| Silicone acrylate particles from ex. 1 | 2.5% |
| B Glycerol | 2.0% |
| Water | 67.6% |

TABLE 4-continued

| Oil-in-water sunscreen lotion according to example 19 | |
|---|---|
| Example | 19 |
| Z Preservative, perfume | q.a. |
| Stability | Good |
| Appearance | White, homogeneous |
| Skinfeel | Gentle, smooth, velvety |

The use examples show that the inventive silicone (meth) acrylate particles can be incorporated into stable cosmetic formulations. The use of these particles allows the sensory properties of cosmetic formulations to be improved significantly without stability and the appearance of the example emulsions deteriorating. More particularly, the incorporation of the composite particles leads to a velvetier, silkier, less dry and less rough skinfeel.

More particularly, the silicone (meth)acrylate particles are also suitable for use in formulations together with pigments, since they significantly improve the typically somewhat rough skinfeel of pigment-containing formulations.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A process for preparing silicone (meth)acrylate particles comprising:
a) obtaining an emulsion composed of water and an organic phase, said organic phase comprising at least one organopolysiloxane which has been modified terminally and/or laterally with (meth)acrylate groups and is of the general formula (I) or mixtures thereof

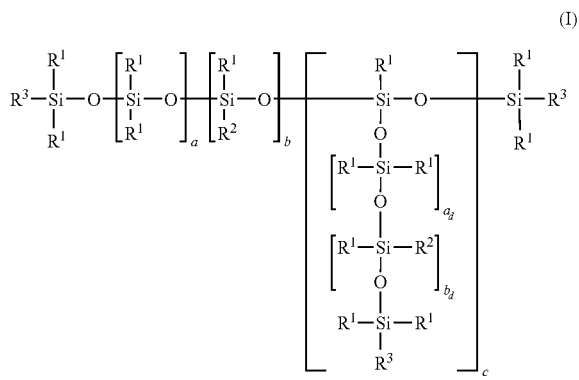

where
R¹=identical or different radicals selected from linear or branched, saturated, monounsaturated or polyunsaturated, linear, cyclic or branched alkyl, alkoxy, polyalkoxy, hydroxyalkyl, hydroxyalkoxy, alkenyl, aryl, aryloxy, hydroxyaryl, hydroxyaryloxy, alkaryl, alkaryloxy, hydroxyalkaryl, hydroxyalkaryloxy, aralkyl, aralkoxy, hydroxyaralkyl or hydroxyaralkoxy radicals which optionally contain one or more ether or ester bridges and have 1 to 20 carbon atoms, R²=identical or different divalent, optionally OH-functionalized hydrocarbon radicals which optionally contain one or more ether or ester bridges, are bonded to the silicon atom via an Si—C linkage or an Si—O—C linkage, have 1 to 20 carbon atoms and to which are bonded, via ester bonds, 1 to 5 acrylic acid and/or methacrylic acid units and optionally monocarboxylic acid units having 2 to 10 carbon atoms, which are free of double bonds capable of polymerization, R³=identical or different R¹ or R² radicals, a=0 to 1000,
b=0 to 200,
c=0 to 200,
$a_d$=0 to 1000,
$b_d$=0 to 200, where
when c>0, at least one of $a_d$ and $b_d$ are >0,
with the proviso that when b and c=0, R³ must not be selected from the same group as R¹, with addition of at least one particulate emulsifier, where the organic phase forms an inner phase of the emulsion, and
b) polymerizing the inner phase to completion in the presence of a free-radical initiator which is added to an outer aqueous phase of the emulsion in a concentration of 0.1 to 40% by weight based on the inner phase.

2. The process according to claim 1, wherein in step a) an emulsion stabilized in a solid state is obtained and the at least one particulate emulsifier used is microscale or nanoscale in at least one dimension and is selected from the group of metal oxides, mixed metal oxides, metal nitrides, metal hydroxides, metal carbonates, metal silicates, silicone resins, silicones and/or organic polymers which are hydrophobized with at least one compound from the group of silanes, siloxanes, quaternary ammonium compounds, cationic polymers and fatty acids or anions thereof, wherein the hydrophobic characteristic is not distributed inhomogeneously over the surface of the particulate emulsifier.

3. The process according to claim 2, wherein in step a) the at least one particulate emulsifier used is microscale or nanoscale in at least one dimension and is selected from the group of metal oxides which are hydrophobized with at least one compound from the group of silanes, siloxanes, and quaternary ammonium compounds.

4. The process according to claim 2, wherein in step a) the at least one particulate emulsifier used is microscale or nanoscale in at least one dimension and is $SiO_2$ which is hydrophobized with at least one compound from the group of silanes, siloxanes, and quaternary ammonium compounds.

5. The process according to claim 2, wherein in step a) the at least one particulate emulsifier used is microscale or nanoscale in at least one dimension and is selected from the group of metal oxides which are hydrophobized with at least one compound from the group of silanes, siloxanes, and quaternary ammonium compounds, and wherein the emulsion obtained in step a) has a mean droplet size of 1 to 100 μm.

6. The process according to claim 2, wherein in step a) the at least one particulate emulsifier used is microscale or nanoscale in at least one dimension and is $SiO_2$ which is hydrophobized with at least one compound from the group of silanes, siloxanes, and quaternary ammonium compounds and wherein the emulsion obtained in step a) has a mean droplet size of 1 to 100 μm.

7. The process according to claim 1, wherein more than 70% of the R¹ radicals in formula (I) are methyl groups.

8. The process according to claim 1, wherein R² in general formula (I) is selected from the group of

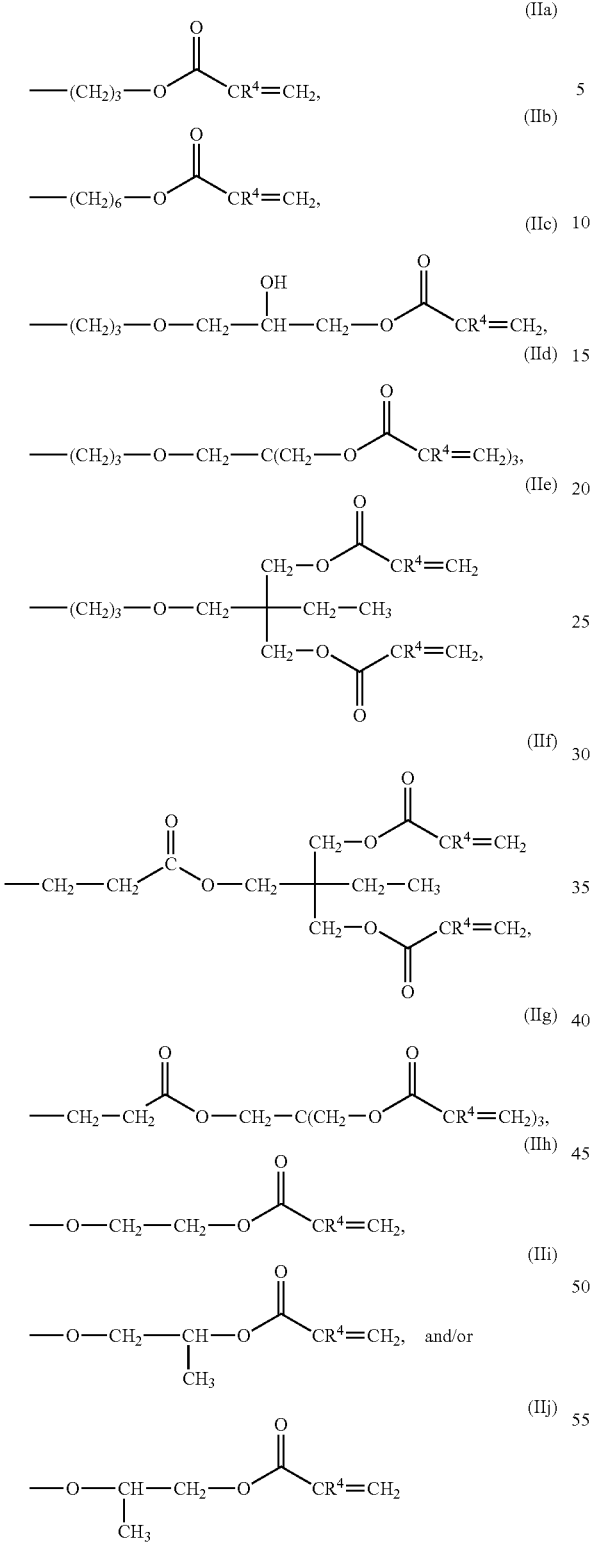

radicals and

R⁴ is hydrogen or a methyl group.

9. The process according to claim 1, wherein said variable a of said silicone (meth)acrylate of formula (I) has a value of 0 to 500.

10. The process according to claim 1, wherein said variable b of said silicone (meth)acrylate of formula (I) has a value of 0 to 100.

11. The process according to claim 1, wherein said variable c of said silicone (meth)acrylate of formula (I) has a value of 0 to 100.

12. The process according to claim 1, wherein said emulsion of step a) further comprises at least one comonomer that is added to the organic phase before step b).

13. The process according to claim 1, further comprising further components that are added to the organic phase in step a).

14. The process according to claim 1, wherein said organic phase further comprises substances which can be released from the particles.

15. The process according to claim 1, wherein the emulsion is prepared in step a) by passing a mixture of organic and aqueous phase through and dispersing the mixture in at least one interaction chamber with a capillary thickness of 50 to 500 μm in a pressure range of 50 to 1000 bar and decompressing the mixture into an outlet reservoir.

16. Silicone (meth)acrylate particles prepared by a process comprising:

a) obtaining an emulsion composed of water and an organic phase, said organic phase comprising at least one organopolysiloxane which has been modified terminally and/or laterally with (meth)acrylate groups and is of the general formula (I) or mixtures thereof

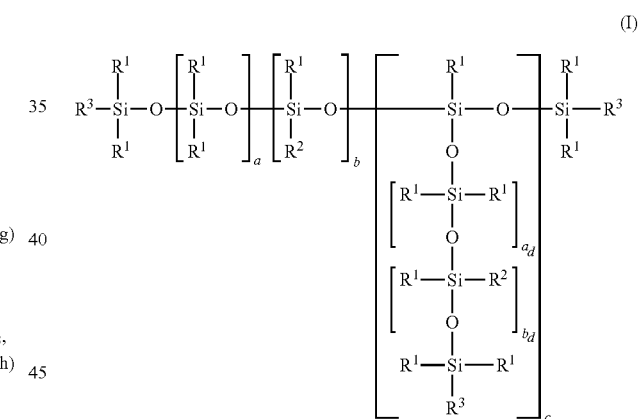

where

R¹=identical or different radicals selected from linear or branched, saturated, monounsaturated or polyunsaturated, linear, cyclic or branched alkyl, alkoxy, polyalkoxy, hydroxyalkyl, hydroxyalkoxy, alkenyl, aryl, aryloxy, hydroxyaryl, hydroxyaryloxy, alkaryl, alkaryloxy, hydroxyalkaryl, hydroxyalkaryloxy, aralkyl, aralkoxy, hydroxyaralkyl or hydroxyaralkoxy radicals which optionally contain one or more ether or ester bridges and have 1 to 20 carbon atoms, R²=identical or different divalent, optionally OH-functionalized hydrocarbon radicals which optionally contain one or more ether or ester bridges, are bonded to the silicon atom via an Si—C linkage or an Si—O—C linkage, have 1 to 20 carbon atoms and to which are bonded, via ester bonds, 1 to 5 acrylic acid and/or methacrylic acid units and optionally monocarboxylic acid units having 2 to 10 carbon atoms, which are free of double bonds capable of polymerization, $R^3$=identical or different $R^1$ or $R^2$ radicals,
a=0 to 1000,
b=0 to 200,
c=0 to 200,
$a_d$=0 to 1000,
$b_d$=0 to 200,
where
when c>0, at least one of $a_d$ and $b_d$ are >0,
with the proviso that when b and c=0, $R^3$ must not be selected from the same group as $R^1$, with addition of at least one emulsifier,
where the organic phase forms an inner phase of the emulsion, and
b) polymerizing the inner phase to completion in the presence of a free-radical initiator which is added to an outer aqueous phase of the emulsion in a concentration of 0.1 to 40% by weight based on the inner phase, wherein the particles further include substances which are released from the particles.

17. A process for preparing silicone (meth)acrylate particles comprising:
a) obtaining an emulsion composed of water and an organic phase, said organic phase comprising at least one organopolysiloxane which has been modified terminally and/or laterally with (meth)acrylate groups and is of the general formula (I) or mixtures thereof

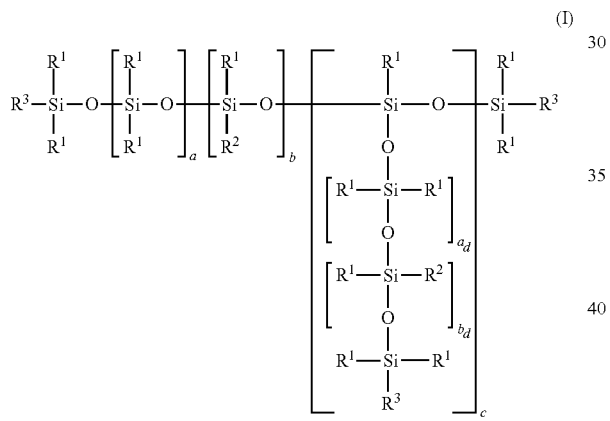

where $R^1$=identical or different radicals selected from linear or branched, saturated, monounsaturated or polyunsaturated, linear, cyclic or branched alkyl, alkoxy, polyalkoxy, hydroxyalkyl, hydroxyalkoxy, alkenyl, aryl, aryloxy, hydroxyaryl, hydroxyaryloxy, alkaryl, alkaryloxy, hydroxyalkaryl, hydroxyalkaryloxy, aralkyl, aralkoxy, hydroxyaralkyl or hydroxyaralkoxy radicals which optionally contain one or more ether or ester bridges and have 1 to 20 carbon atoms, $R^2$=identical or different divalent, optionally OH-functionalized hydrocarbon radicals which optionally contain one or more ether or ester bridges, are bonded to the silicon atom via an Si—C linkage or an Si—O—C linkage, have 1 to 20 carbon atoms and to which are bonded, via ester bonds, 1 to 5 acrylic acid and/or methacrylic acid units and optionally monocarboxylic acid units having 2 to 10 carbon atoms, which are free of double bonds capable of polymerization, $R^3$=identical or different $R^1$ or $R^2$ radicals,
a=0 to 1000,
b=0 to 200,
c=0 to 200,
$a_d$=0 to 1000,
$b_d$=0 to 200,
where
when c>0, at least one of $a_d$ and $b_d$ are >0,
with the proviso that when b and c=0, $R^3$ must not be selected from the same group as $R^1$, with addition of at least one emulsifier, where the organic phase forms an inner phase of the emulsion, and
c) polymerizing the inner phase to completion in the presence of a free-radical initiator which is added to an outer aqueous phase of the emulsion in a concentration of 0.1 to 40% by weight based on the inner phase, wherein said organic phase further comprises substances which can be released from the particles.

18. A composition of matter comprising silicone (meth)acrylate particles having a core-shell structure, whereas said shell is formed of a particulate emulsifier and surrounds said core comprises a polymerised silicone (meth)acrylate.

19. The composition of matter of claim 18 wherein said composition of matter is a dispersion of said silicone (meth)acrylate particles in aqueous or organic media.

20. The composition of matter of claim 18 wherein said composition of matter is a coating, adhesive or sealant material, a polymer, a defoamer, wetting and/or levelling aid, a cosmetic, a care product, a medical product, a pharmaceutical, a washing composition, a cleaning and/or detergent composition, a hydrophobizing agent, a lubricant or a release agent.

21. The composition of matter according to claim 18 wherein said shell is modified with substances selected from the group consisting of organic ammonium ions, cationic polymers, cationic siloxanes, polyacrylates, carboxylic acids, carboxylic acid anions, chelating agents, diketones, siloxanes and condensed silanes.

* * * * *